(12) United States Patent
Gross et al.

(10) Patent No.: US 8,735,463 B2
(45) Date of Patent: May 27, 2014

(54) SELF-HEALING DENTAL COMPOSITES AND RELATED METHODS

(75) Inventors: Stephen M. Gross, Omaha, NE (US); Mark A. Latta, Omaha, NE (US)

(73) Assignee: Creighton University, Omaha, NE (US)

(*) Notice: Subject to any disclaimer, the term of this patent is extended or adjusted under 35 U.S.C. 154(b) by 1655 days.

(21) Appl. No.: 11/809,248

(22) Filed: May 31, 2007

(65) Prior Publication Data

US 2008/0300340 A1 Dec. 4, 2008

(51) Int. Cl.
*A61K 6/083* (2006.01)
*A61K 6/08* (2006.01)
*C08K 9/10* (2006.01)

(52) U.S. Cl.
USPC ........... 523/113; 523/115; 523/201; 523/202; 523/205; 523/207; 433/228.1

(58) Field of Classification Search
USPC ......... 523/115, 116, 118, 113, 201, 202, 205, 523/207; 433/228.1
See application file for complete search history.

(56) References Cited

U.S. PATENT DOCUMENTS

| | | | |
|---|---|---|---|
| 5,716,709 A | 2/1998 | Ferguson et al. | |
| 6,022,590 A | 2/2000 | Ferguson et al. | |
| 6,075,068 A * | 6/2000 | Bissinger | 523/116 |
| 6,075,072 A | 6/2000 | Guilbert et al. | |
| 6,121,344 A | 9/2000 | Angeletakis et al. | |
| 6,143,919 A | 11/2000 | Shen et al. | |
| 6,147,136 A * | 11/2000 | Bissinger | 523/116 |
| 6,221,931 B1 | 4/2001 | Sakuma et al. | |
| 6,264,741 B1 | 7/2001 | Brinker et al. | |
| 6,300,390 B1 | 10/2001 | Angeletakis | |
| 6,306,927 B1 | 10/2001 | Blackwell et al. | |
| 6,313,192 B1 | 11/2001 | Anstice et al. | |
| 6,399,037 B1 | 6/2002 | Pflug et al. | |
| 6,410,765 B1 | 6/2002 | Wellinghoff et al. | |
| 6,447,907 B1 | 9/2002 | Wolter et al. | |
| 6,518,330 B2 | 2/2003 | White et al. | |
| 6,575,752 B1 | 6/2003 | Pflug et al. | |
| 6,593,395 B2 | 7/2003 | Angeletakis et al. | |
| 6,602,932 B2 | 8/2003 | Feldheim et al. | |
| 6,669,476 B2 | 12/2003 | Prestipino et al. | |
| 6,693,143 B2 | 2/2004 | Pflug | |
| 6,695,617 B1 | 2/2004 | Wellinghoff et al. | |
| 6,696,585 B1 | 2/2004 | Wellinghoff et al. | |
| 6,730,156 B1 | 5/2004 | Windisch et al. | |
| 6,743,936 B1 | 6/2004 | Wellinghoff et al. | |
| 6,787,629 B2 | 9/2004 | Jia et al. | |
| 6,794,472 B2 | 9/2004 | Harris et al. | |
| 6,808,461 B2 | 10/2004 | Harris et al. | |
| 6,835,394 B1 | 12/2004 | Discher et al. | |
| 6,855,197 B2 | 2/2005 | Su et al. | |
| 6,855,749 B1 | 2/2005 | Yadav et al. | |
| 6,858,659 B2 | 2/2005 | White et al. | |
| 6,858,660 B1 | 2/2005 | Scheifers et al. | |
| 6,869,701 B1 | 3/2005 | Aita et al. | |
| 6,890,968 B2 | 5/2005 | Angeletakis et al. | |
| 6,899,948 B2 | 5/2005 | Zhang et al. | |
| 6,913,825 B2 | 7/2005 | Ostafin et al. | |
| 6,916,872 B2 | 7/2005 | Yadave et al. | |
| 6,932,602 B2 | 8/2005 | Hamilton | |
| 2002/0132875 A1 | 9/2002 | Stadtmueller | |
| 2004/0007784 A1 | 1/2004 | Skipor et al. | |
| 2004/0039079 A1 | 2/2004 | Qian | |
| 2005/0003016 A1 | 1/2005 | Discher et al. | |
| 2005/0159510 A1 * | 7/2005 | Smolak et al. | 523/216 |
| 2005/0189537 A1 | 9/2005 | Scheifers et al. | |
| 2005/0250878 A1 | 11/2005 | Moore et al. | |
| 2006/0004158 A1 * | 1/2006 | Moszner et al. | 526/171 |
| 2006/0111469 A1 * | 5/2006 | White et al. | 523/200 |
| 2006/0171900 A1 | 8/2006 | Angeletakis | |

OTHER PUBLICATIONS

Bouchemal et al. "Synthesis and characterization of polyurethane and poly(ether urethane) nanocapsules using a new technique of interfacial polycondensation combined to spontaneous emulsification." *Int J. Pharm.* Jan. 9, 2004; vol. 269(1) pp. 89-100 PubMed.

Kulkarni, et al. "Urea-formaldehyde nanocapsules for the controlled release of diclofenac sodium." *Journal of Microencapsulation.* 2000 vol. 17 No. 4, pp. 449-458. © 2000 Taylor & Francis Ltd.

Moszner et al. "Nanotechnology for dental composites"; *International Journal of Nanotechnology*, 2004, vol. 1, Nos. 1/2 pp. 130-156. © 2004 Inderscience Enterprises Ltd.

Yuan, et al. "Photocleavable Microcapsules Build from Photoreactive Nanospheres." *Langmuir* 2005 vol. 21, pp. 9374-9380. © 2005 American Chemical Society.

Peyratout et al. "Tailor-Made Polyelectrolyte Microcapsules: From Multilayers to Smart Containers." *Angew Chem Int. Ed.* 2004, vol. 43 pp. 3762-3783. © 2004 Wiley-VCH Verlag GmbH & Co. KGaA, Weinheim.

Tan, et al. "Bionanotechnology Based on Silica Nanoparticles." *Medical Research Reviews*, 2004 vol. 24, No. 5, pp. 621-638. © 2004 Wiley Periodicals, Inc.

Bush et al. "Ceramic Micro-Particles Synthesised using Emulsion and Sol-Gel Technology: An Investigation into the Controlled Release of Encapsulants and the Tailoring of Micro-Particle Size." *Journal of Sol-Gel Science and Technology* 2004 vol. 32, pp. 85-90. © 2004 Kluwer Academic Publishers.

(Continued)

*Primary Examiner* — Michael Pepitone
(74) *Attorney, Agent, or Firm* — Advent, LLP

(57) ABSTRACT

Dental restorative composites having self-healing capabilities to repair discontinuities in the composite are provided. Dental restorative composites according to the present invention include a microsphere that encapsulates a monomer. When a fracture occurs, the microsphere is ruptured and the monomer fills the fracture. Depending on the monomer present in the microsphere, it is polymerized by a polymerization initiator or by an olefin metathesis catalyst present in the dental restorative composite. Self-healing dental restorative composites provide increased resistance to fracturing, and thus remain substantially intact for a longer period of time, preserving the remedial integrity of the dental repair or reconstruction.

10 Claims, No Drawings

(56) References Cited

OTHER PUBLICATIONS

White, et al. "Autonomic healing of polymer composites." *Nature.* Feb. 15, 2001 vol. 409, pp. 794-797. © 2001 Macmillian Magazines Ltd.

Lin, et al. "Self-directed self-assembly of nanoparticle/copolymer mixtures." *Nature* Mar. 3, 2005 vol. 434 pp. 55-59 © 2005 Nature Publishing Group.

Lee et al. "Using nanoparticles to create self-healing composites." *Journal of Chemical Physics*, Sep. 15, 2004 vol. 121, No. 11, pp. 5531-5540 © 2004 American Institute of Physics.

Smith, et al. "Healing Surface Defects with Nanoparticle-Filled Polymer Coatings: Effect of Particle Geometry." *Macromolecules* 2005, vol. 38, pp. 10138-10147 © 2005 American Chemical Society.

Wohlgemuth, et al. "Improved preparation and physical studies of polybutylcyanacrylate nanocapsultes." *Journal of Microencapsulation*, 2000, vol. 17, No. 4, pp. 437-448 © Taylor & Francis Ltd.

\* cited by examiner

SELF-HEALING DENTAL COMPOSITES AND RELATED METHODS

FIELD OF THE INVENTION

The present invention relates to dental repairs and reconstructions, and more particularly to dental restorative composites having self-healing characteristics, or capability to autonomically resolve discontinuities occurring in the composite. The present invention also relates to methods of forming the self-healing composite materials and methods of use thereof.

BACKGROUND OF THE INVENTION

At one time, metal-based amalgams, then porcelain or other ceramic materials were used in a variety of remedial dental procedures. Now, synthetic composites are used as practical alternatives to these materials for such procedures. A composite is a polymer, otherwise referred to as a resin, which has at least one additive. An additive can be anything added to the polymer or resin to impart a desired property. The composite generally starts out as a paste or liquid and begins to harden when it is activated, either by adding a catalyst, adding water or another solvent, or photoactivation. Advantageously, synthetic composites provide an aesthetically more natural appearance versus porcelain or other ceramic materials.

Synthetic composites are typically made from complex mixtures of multiple components. Synthetic composites must be completely dissolvable in a fluid vehicle, yet remain flowable and viscous; undergo minimal thermal expansion during polymerization; be biocompatible with surrounding surfaces of tooth enamel and colloidal dentin; and, have aesthetic similarity to natural dentition in terms of color tone and polishable texture. Furthermore, the synthetic composite must have sufficient mechanical strength and elasticity to withstand ordinary compressive occlusive forces, without abnormal wearing and without causing abrasion to dentinal surfaces.

The different varieties of synthetic composites may be approximately divided into three main groups of products: synthetic resin-based dental composites, glass-based dental composites, and hybrid dental composites.

A synthetic resin-based dental composite typically comprises several monomers combined together. A monomer is a chemical that can be bound as part of a polymer. The synthetic resin-based dental composite includes other materials, such as silicate glass or processed ceramic that provides an essential durability to the composite. These materials may also be made from an inorganic material, consisting of a single type or mixed variety of particulate glass, quartz, or fused silica particles. Using differing types of inorganic materials, with differing diameter sizes or size mixtures, results in differing material characteristics.

Glass-based dental composites are made from a glass particles, such as powdered fluoroaluminosilicate, dissolved in an aqueous polyalkenoate acid. An acid/base reaction occurs spontaneously, causing precipitation of a metallic polyalkenoate, which subsequently solidifies gradually. The glass particles may be made from silicate, such as silicone dioxide or aluminum silicate, but may also include an intermixture of barium, borosilicate, alumina, aluminum/calcium, sodium fluoride, zirconium, or other inorganic compounds. Some of the earlier glass-based composites were formulated to contain primarily a mixture of acrylic acid and itaconic acid co-monomers. However, more recently such hybrid products are modified to include other polymerizable components, such as HEMA or BisGMA.

Hybrid composites are the third category of synthetic dental composites. Hybrid composites combine glass particles with one or more polymers. Hybrid composites may comprise water-soluble polymers other than polyalkenoate, such as hydroxyethyl methacrylate (HEMA) and other co-polymerizing methacrylate-modified polycarboxylic acids, which are catalyzed by photo activation. Other hybrid composites may be modified to include polymerizable tertiary amines, catalyzed by reaction with peroxides.

Synthetic dental composites are increasingly used more often for dental procedures, such as restoration and repair. Restoration and repair includes, for example, fillings, crowns, bridges, dentures, orthodontic appliances, cements, posts and ancillary parts for dental implants to name a few. Most common, synthetic dental composites are used for anterior Class III and Class V reconstructions, for smaller size Class I and Class II molar reconstructions, for color-matching of cosmetic veneers, and for cementing of crowns and overlays. Nonetheless certain disadvantages of these materials have been noted. For example, the trace amounts of unconverted monomers and/or catalyst that may remain within the composite and, if subsequently absorbed systemically in humans, may be potentially physiologically harmful.

Another major drawback associated with synthetic composites is that they tend to wear more rapidly, especially when placed in appositional contact with load-bearing dental surfaces, a deficiency that often limits the purposeful use of such materials primarily to repair of defects within anterior maxillary or readily visible mandibular surfaces.

Perhaps the most significant disadvantage associated with synthetic composites is that they have a comparatively lower resistance to fracture. Even relatively minor surface discontinuities within the composite, whether occurring from injurious trauma or occlusive stress, may progressively widen and expand, eventually resulting in partial or complete disintegration of the reconstruction or repair. This greater susceptibility to fracture is thought to be correlated with the dental reconstruction or repair.

Fracture susceptibility is also correlated with the proportional volume of the amount of synthetic composite required, or the lesser fraction of intact enamel and dentinal tooth material that remains available, prior to reconstruction or repair. It is well established from studies of the "cracked tooth syndrome" that once a damaging fracture has occurred, tooth loss may be almost inevitable, especially for carious teeth that have been previously filled. An improved synthetic composite having greater resistance to fracture would be significantly advantageous.

Synthetic composites having self-healing characteristics are known in the art, as illustrated for example in U.S. Pat. Nos. 6,518,330 and 6,858,659, describing self-repair of a polyester material containing unreacted amounts of cyclopentadiene (DCPD) monomer stored within a polyester matrix resin, as sequestered within polyoxymethyleneurea (PMU) microcapsules. From a fracturing mechanical stress sufficient to cause rupturing of one or more microcapsule, the monomer is reactively released. As the monomer contacts the polyester matrix, a polymerization occurs. The in situ polymerization occurs as a result of a ruthenium-based Grubbs catalyst or Schrock catalyst, which may be incorporated into the matrix. Alternatively, the catalyst may be stored within a fraction of separately prepared microcapsules, or may be contained within the same material comprising the microcapsule outer wall.

Although these patents disclose a composite having self-healing characteristics, there is still a demand for dental restorative composites having self-healing characteristics, or capability to autonomically resolve discontinuities occurring in the composite as well as methods of making such composites. The present invention satisfies this demand.

SUMMARY OF THE INVENTION

A dental restorative composite is a polymer, otherwise referred to as resin. Common components of a dental restorative composite typically comprise a monomer, glass filler, coupling agent, polymerization initiator (or photosensitizer), accelerator, polymerization inhibitor, and UV inhibitor.

A monomer are molecules, when combined together form macromolecules. A glass filler is added to achieve desired physical properties of the composite, for example reduction of shrinkage of the composite during polymerization. A coupling agent allows the glass filler to chemically bond with monomers and a polymerization initiator allows the monomer to become a polymer. Monomers are typically polymerized after application to the tooth or other dental appliance. A polymerization initiator includes a catalyst or photosensitizer, which is the process of activating a substance by means of radiant energy, especially light. An accelerator increases the rate of polymerization, or rate at which a monomer converts to a polymer. The inhibitors provide increased storage and shelf-life by preventing premature polymerization.

A primary object of the present invention is to provide a synthetic dental restorative composite that has self-healing characteristics, or capability to autonomically resolve discontinuities, including fractures, discontinuities, fissures, or other minor imperfections that might otherwise expand and propagate, and eventually degrade the mechanical and structural integrity of the dental composite.

An object of the present invention is to provide a dental restorative composite made of materials that if absorbed systemically in humans would not be physiologically harmful.

Another object of the present invention is to provide a dental restorative composite that wears slowly compared to existing dental composites and has a greater resistance to fracture.

Another object of the present invention is to provide a dental restorative composite with one or more microspheres encapsulating a monomer.

According to another embodiment of the present invention, a catalyst is added to the dental restorative composite to polymerize the encapsulated monomer. When a fracture ruptures the microsphere, which contains a monomer, the catalyst polymerizes the encapsulated monomer.

Yet another embodiment of the present invention includes at least two microspheres: one microsphere that encapsulates a polymer along with a crosslinking agent and a second microsphere that encapsulates a catalyst. This embodiment relies on a crosslinking reaction and is biocompatible such that the reaction between the polymer, crosslinking agent and catalyst can take place at body temperature. The polymers according to this embodiment include a cure site, for example polyesters, unsaturated polyesters, alkyds, phenolic polymers (including resoles and novolacs), amino plastics, epoxy resins, polyurethanes, polysulfides and polysiloxanes, such as hydroxyfunctional polysiloxanes, that include hydroxyfunctional-polydichlorodimethylsiloxane, hydroxyfunctional-polydichloromethylphenylsiloxane, hydroxyfunctional-polydichlorodiphenylsiloxane and hydroxyfunctional-polydimethylsiloxane. The crosslinking agent, for example, silane crosslinking agents, provides the ability to autonomically heal a discontinuity in the composite when activated by the catalyst. Types of silane crosslinking agents include methylytrimethoxysilane, methyltriethoxysilane, tetramethoxysilane, tetraethoxysilane, tetrapropoxysilane, methyltris(methylethylketoxime)silane, methyltris(methylisobutylketoxime)silane, dimethyldi(ethylmethylketoxime)silane, trimethyl(ethylmethylketoxime)silane, vinyltris(ethylmethylketoxime)silane, methylvinyl(dimethylethylketoxime)silane, methylvinyldi(etlylmethylketoxime), methylvinyldi(cyclohexanoneoxime), vinyltris(methylisobutylketoxime)silane, phenyltris(methylethylketoxime)silane, methyltriacetoxysilane, tetraacetoxysilane Compounds to catalyze the crosslinking reaction include tin salts such as organotin catalysts, which include stannous octooate, dialkyl dicarboxylate or dibutyl tin dilaurate, platinum compounds such as chloroplatinic acid, and hydride-functional siloxanes.

Another object of the present invention is to provide a dental restorative composite that requires no external stimuli to resolve fractures. Upon fracture of the composite, a microsphere ruptures releasing a monomer that is polymerized to bond the fracture closed.

According to one embodiment of the present invention, a microsphere that encapsulates a monomer provides the ability to autonomically heal a discontinuity in the composite. The encapsulated monomer is one of the typical monomers normally used in dental restoratives as discussed herein. An applied dental restorative may undergo a fracture during its lifetime. The fracture ruptures the microsphere, which contains a monomer. The monomer fills the fracture and is polymerized by the polymerization initiator already present in the dental restorative.

In this embodiment, the encapsulated monomer is not limited to monomers typically used in the formulation of dental restorative materials. For example, this embodiment can use an encapsulated monomer that is known to undergo olefin metathesis along with a catalyst that is an olefin metathesis catalyst.

An additional object of the present invention is to provide a method for the formulation of a self-healing dental restorative composite that may be used for accomplishing dental repair or reconstruction of a damaged dental restorative composite.

As further additional objects of the invention, the dental restorative composites using monomers with a self-healing capability could be equally applicable and appropriate, for example, monomers used in other types of reparative, reconstructive, protective, or palliative procedures, such as minor fillings, crowns, bridges, implants, prosthetics, dentures, bite plates, mouthpieces, orthodontic brackets and parts or subcomponents ancillary thereto, or in fact virtually any type of synthetic material as may be placed by a dentist or fabricated in a dental laboratory.

Among the advantages of the dental restorative composite of the present invention are those that result from the improved material characteristics that confer greater resistance to fracturing, increased flexural strength and wear resistance, and better durability and toughness, as compared to materials made from conventional dental resins. It is considered that similar material advantages might be realized for a wide spectrum of various types of dental restorative composites, having particularized purposes and composite formulations that are otherwise separately distinct.

Microspheres, or encapsulated particles, according to the present invention require sufficient resilience to withstand the reconstructive dental procedure, and must remain impermeable within the fully polymerized composite, while at the same time remaining susceptible to rupture of the microsphere and release of its contents.

Methods for constructing microspheres may by physical or chemical. Physical methods of manufacturing microspheres include pan coating, air-suspension coating, centrifugal extrusion, vibrational nozzle and spray-drying. Chemical methods of manufacturing microspheres are known as polymerization. Polymerization is the bonding of monomers to form a microsphere. Polymerization of chemicals generally includes interfacial polymerization, in-situ polymerization and matrix polymerization. In interfacial polymerization, at least two monomers are dissolved separately in immiscible liquids. Upon interface between the liquids, rapid reaction occurs creating a thin shell or wall of the microsphere. In-situ polymerization is the direct polymerization of a single monomer carried out on the particle surface. Matrix polymerization, a core material is imbedded during formation of the microsphere.

Encapsulated particles might also be prepared by using sol-gel techniques, by aqueous or organic solution precipitation synthesis methods, olefin metathesis polymerization including cross metathesis, ring closing metathesis, enzyme metathesis, ring opening metathesis, ring opening metathesis polymerization, acyclic metathesis, alkyne metathesis, alkane metathesis, alkene metathesis and acetylenic metathesis, or complex coacervation, interfacial polymerization, or by other methods known in the art.

Regarding other microencapsulation technologies, the prior art is considered to contain at least several methodologies that may be applicable. Complex coacervation processes occurring in aqueous solution involve chemical reactions between dissolved cationic and anionic polymers such as gelatin and gum arabic, whereby the polymers aggregate into a concentrated phase, which can be centrifuged or otherwise separated away from the aqueous supernatant. A water-immiscible core material added slowly to the aggregate then becomes coated by the coacervate aggregate, such that thin films of polymer may then surround dispersed droplets of the added core material, with the polymer material then solidifying to form the encapsulating outer shell. However, microspheres formed by this method may not sufficiently durable to remain stable within an aqueous environment.

Microencapsulation can also be achieved by the multilayering of polyelectrolytes, as described for example in U.S. Pat. No. 6,602,932 and U.S. Pub. No. 2005/0037050, may produce nano-sized capsules. However, these may be primarily adaptable for purposes of drug delivery and controlled release, with such capsules having exceedingly thin (50 nm) outer shells that do not provide sufficiently rigid outer shell structure.

More effective adaptable microencapsulation may be obtained from interfacial polymerization, a process wherein monomers are dissolved with the core material, and the combined solution is then mixed with an aqueous phase solute, to form an emulsion or polymer material. A catalytic material added to the polymer material to initiate polymerization that occurs primarily at the surface of the polymer material. As polymerization proceeds, the polymer material hardens to form an outer encapsulating shell surrounding the core material contents. As described previously, microencapsulation involving in-situ polymerization are distinct from interfacial polymerization processes to the extent that the polymer material that forms the encapsulating shell and the core material to be contained are not pre-mixed before combining, so that the polymer material may undergo polymerization to form a shell while the core material remains unreactive. Methods for forming microsphere shells by in-situ condensation of formaldehyde and an amine are described in U.S. Pat. Nos. 4,001,140; 4,087,376; 4,089,802; and 4,100,103 which describe processes for producing microspheres having diameter sizes of approximately 5 to 15 microns. Similar processes described in U.S. Pat. Nos. 4,353,809 and 4,409,156 may produce microspheres of approximately the same size diameter. Microspheres made from such methods may be adaptable for use in dental procedures, as shown in the prior art described in U.S. Pat. No. 6,932,602.

It will of course be understood that the aspects and objectives of the invention are various, and need not be all present in any given embodiment of the invention. The features, advantages and accomplishments of the invention will be further appreciated and understood upon consideration of the following detailed description of embodiments of the invention.

DETAILED DESCRIPTION

Common components of a dental restorative composite typically comprise a monomer, glass filler, coupling agent, polymerization initiator, accelerator, polymerization inhibitor, and UV inhibitor.

According to one embodiment of the present invention, adding a microsphere that encapsulates a monomer to the dental restorative composite provides the ability to autonomically heal the composite in the event of a fracture. Upon rupture of the microsphere, the encapsulated monomer forms a polymer when in contact with a polymerization initiator.

The present invention includes a dental restorative composite containing monomers that form polymers, such as a homopolymer or copolymer. A homopolymer is a polymer which is formed from only one type of monomer. This is in contrast to a copolymer where the polymer contains at least two monomers.

The encapsulated monomer is one of the typical monomers normally used in dental restorative composites, for example, modified dimethacrylates such as 2,2-bis[4-(2-hydroxy-3-methacryloyloxypropoxy)phenyl]propane (Bis-GMA), dimethacryloxyethyl 2,2,4-trimethylhexamethylene diurethane (UDMA), and 1,6-bis-[2-methacryloxy-ethoxycarbonylamino]-2,2,4-trimethylhexane (UEDMA). Other types of synthetic resins appropriately useful for dental repairs and restorations include triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DEGDMA), hexanediol dimethacrylate (HDMA), hexanediol diacrylate (HDDA), trimethylolpropanetriacrylate (TMPTA), trimethylolpropanetrimethacrylate (TMPTMA), ethoxylated trimethylolpropanetriacrylate (EOTMPTA) and ethoxylated bisphenol A dimethacrylate (EBPADMA). Another type of encapsulated monomer could include a silorane such as bis-3,4-epoxycyclohexylethylphenylmethylsilane and 3,4-epoxycyclohexylethylcyclopolymethylsiloxane.

Other monomers used in dental restorative composites include isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2, 4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa- (meth)acrylate; tetrahydrofurfuiryl(meth)acrylate; bis[1-(2-acryloxy)]-p-ethoxyphenyldimethylmethane; bis[1-(3-acryloxy-2-hydroxy)]-p-propoxyphenyidimethylmethane; 2,2,4-trimethylhexamethylene diisocyanate; tris-hydroxyethyl-isocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional(meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional(meth)acrylate polysiloxanes, defined as products resulting from hydrolytic polycondensation of one or more of the following silanes: bis[2-(2-(methacryloyl oxyethoxycarbonyl)ethyl)]-3-¬ triethoxysily-lpropyl amine, bis[2-(2(1)-(methacryloyloxypropoxycarbonyl)ethyl)]-3-triet-hoxysilylpropyl amine, 1,3(2)-dimethacryloyloxypropyl-[3-(3-triethoxysilyl-propyl)aminocarbonyl]propionate, 1,3(2)-dimethacryloyloxypropyl-[4-(3-triethoxysilyl propyl)aminocarbonyl]butyrate, 1,3(2)-dimethacryloyloxypropyl-[-4-(3-triethoxysilylpropyl)-N-¬ ethylaminocarbonyl] butyrate, 3-[1,3(2)-dimethacryloyl oxypropyl)-2(3)-oxycarbonylamido]¬ propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids.

It is contemplated that any formulation for a dental restorative composite may include multiple monomers, including any combination of the foregoing.

An applied dental restorative composite may undergo a fracture during its lifetime. The fracture ruptures the microsphere, which contains a monomer. The monomer fills the fracture and is polymerized by the polymerization initiator already present in the dental restorative. Types of polymerization initiators include, for example, catalyst or photosensitizer.

According to another embodiment of the present invention, adding a catalyst to the dental restorative composite that can polymerize the encapsulated monomer also provides the ability to autonomically heal. When a fracture ruptures the microsphere, which contains a monomer, the catalyst polymerizes the encapsulated monomer.

In this embodiment, the encapsulated monomer is not limited to monomers typically used in the formulation of dental restorative materials. For example, this embodiment can use an encapsulated monomer that is known to undergo olefin metathesis along with a catalyst, for example a metathesis catalyst, such as an olefin metathesis catalyst, a Grubbs' catalyst. A catalyst is anything that when contacted or mixed with the monomer will form a polymer.

Monomers known to undergo olefin metathesis include, but are not limited to, cyclopentadienes, norbornenes, norbornadienes, 7-oxonorbornenes, azanorbornenes, cyclobutenes, cyclooctenes, cyclooctadienes, cyclooctatetraenes, acyclic dienes, acetylenes and all derivatives thereof. For example, it is contemplated that any monomer of the class of acyclic dienes, such as 1,9-decadiene, is preferably utilized for embodiments in accordance with the present invention. In addition, it is also contemplated that monomers and derivates such as o(trimethylsilyl)phenylacetylene can be utilized.

Those of ordinary skill in the art will appreciate that the various derivates of the monomers discussed herein can be utilized with embodiments in accordance with the present invention. Indeed, it is contemplated that monomers for use in accordance with the present invention could preferably be substituted in a number of ways. For example, cyclobutene can have a halogen or an alkyl substitute. As such, those of ordinary skill in the art would understand that 3-methylcyclobutene or 3-chlorocyclobutene could also be utilized in addition to cyclobutene itself.

Yet another embodiment of the present invention includes at least two microspheres: one microsphere that encapsulates a polymer along with a crosslinking agent and a second microsphere that encapsulates a catalyst. This embodiment relies on a crosslinking reaction and is biocompatible such that the reaction between the polymer, crosslinking agent and catalyst can take place at body temperature. The polymers according to this embodiment include a cure site, for example polyesters, unsaturated polyesters, alkyds, phenolic polymers (including resoles and novolacs), amino plastics, epoxy resins, polyurethanes, polysulfides and polysiloxanes, such as hydroxyfunctional polysiloxanes, that include hydroxyfunctional-polydichlorodimethylsiloxane, hydroxyfunctional-polydichloromethylphenylsiloxane, hydroxyfunctional-polydichlorodiphenylsiloxane and hydroxyfunctional-polydimethylsiloxane. The crosslinking agent, for example, silane crosslinking agents, provides the ability to autonomically heal a discontinuity in the composite when activated by the catalyst. Types of silane crosslinking agents include methyltrimethoxysilane, methyltriethoxysilane, tetramethoxysilane, tetraethoxysilane, tetrapropoxysilane, methyltris(methylethylketoxime)silane, methyltris(methylisobutylketoxime)silane, dimethyldi(ethylmethylketoxime)silane, trimethyl(ethylmethylketoxime)silane, vinyltris(ethylmethylketoxime)silane, methylvinyl(dimethylethylketoxime)silane, methylvinyidi(etlylmethylketoxime), methylvinyldi(cyclohexanoneoxime), vinyltris(methylisobutylketoxime)silane, phenyltris(methylethylketoxime)silane, methyltriacetoxysilane, tetraacetoxysilane Compounds to catalyze the crosslinking reaction include tin salts such as organotin catalysts, which include stannous octooate, dialkyl dicarboxylate or dibutyl tin dilaurate, platinum compounds such as chloroplatinic acid, and hydride-functional siloxanes.

Those of ordinary skill in the art will appreciate that the various derivates of polymers, crosslinking agents, and catalysts can be utilized with embodiments in accordance with the present invention.

In addition, as those of ordinary skill in the art would appreciate, in addition to the homopolymers utilizing the above listed monomers, it is contemplated that embodiments in accordance with the present invention utilize copolymers of the monomers of the classes listed above. For example, it is contemplated that a cyclopentadiene-cyclobutene copolymer may be more advantageous for a particular application for use with embodiments of the present invention.

Following are examples of dental restorative composites with self-healing characteristics:

Example 1

A composition for a dental resin composite with self-healing capabilities is described as follows. A resin mixture (16 wt % total) was first made by combining bisphenol-A-glycidyi-dimethacrylate (Bis-GMA) resin with triethylene glycol dimethacrylate (TEGDMA) resin in a 7/3 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, dicyclopentadiene filled microspheres 2.5 wt % and Grubb's Catalyst 0.5 wt %.

Example 2

A composition for a dental resin composite with self-healing capabilities is described as follows. A resin mixture (16 wt % total) was first made by combining Bis-GMA resin with TEGDMA resin in a 7/3 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 61 wt %, fumed silica 7 wt %, dicyclopentadiene filled microspheres 14 wt % and Grubb's Catalyst 2 wt %.

Example 3

A composition for a dental resin composite with self-healing capabilities is described as follows. A resin mixture (16 wt % total) was first made by combining urethane dimethacrylate (UDMA) resin, Bis-GMA resin with TEGDMA resin in a 3/3/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, dicyclopentadiene filled microspheres 2.5 wt % and Grubb's Catalyst 0.5 wt %.

Example 4

A composition for a dental resin composite with self-healing capabilities is described as follows. A resin mixture (16 wt % total) was first made by combining urethane dimethacrylate (UDMA) resin, Bis-GMA resin with TEGDMA resin in a 3/3/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 61 wt %, fumed silica 7 wt %, dicyclopentadiene filled microspheres 14 wt % and Grubb's Catalyst 2 wt %.

Example 5

A composition for a dental resin composite with self-healing capabilities is described as follows. A resin mixture (16 wt % total) was first made by combining UDMA resin with TEGDMA resin in a 4/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, dicyclopentadiene filled microspheres 2.5 wt % and Grubb's Catalyst 0.5 wt %.

Example 6

A composition for a dental resin composite with self-healing capabilities is described as follows. A resin mixture (16 wt % total) was first made by combining UDMA resin with TEGDMA resin in a 4/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 61 wt %, fumed silica 7 wt %, dicyclopentadiene filled microspheres 14 wt % and Grubb's Catalyst 2 wt %.

Example 7

A composition for a dental resin composite with self-healing capabilities is described as follows. A resin mixture (16 wt % total) was first made by combining a cycloaliphatic epoxy resin such as 3,4-epoxycyclohexylmethyl-3,4-epoxycyclohexanecarboxylate with a polyol such as poly(tetrahydrofuran) such that ratio of epoxy groups to polyol groups was 6:1. A photosensitizer (camphoroquinone) was added at 0.75 wt % of the total composition. An initiator (4-octyloxy-phenyl-phenyl iodonium hexafluoroantimonate) was added at 1.5 wt % of the total composition. An inhibitor (4-methoxyphenol) was added at 0.05 wt % of the total composition. The resin, photosensitizer, initiator and inhibitor were combined in a flask and mixed at 50° C. Upon homogenization, the above resin blend was mixed with the following fillers (84 wt % total): silanated strontium glass 71 wt %, fumed silica 10 wt %, dicyclopentadiene filled microspheres 2.5 wt % and Grubb's Catalyst 0.5 wt %.

Example 8

A composition for a dental resin composite with self-healing capabilities is described as follows. A resin mixture (16 wt % total) was first made by combining a cycloaliphatic epoxy resin such as 3,4-epoxycyclohexylmethyl-3,4-epoxycyclohexanecarboxylate with a polyol such as poly(tetrahydrofuran) such that ratio of epoxy groups to polyol groups was 6:1. A photosensitizer (camphoroquinone) was added at 0.75 wt % of the total composition. An initiator (4-octyloxy-phenyl-phenyl iodonium hexafluoroantimonate) was added at 1.5 wt % of the total composition. An inhibitor (4-methoxyphenol) was added at 0.05 wt % of the total composition. The resin, photosensitizer, initiator and inhibitor were combined in a flask and mixed at 50° C. Upon homogenization, the above resin blend was mixed with the following fillers (84 wt % total): silanated strontium glass 61 wt %, fumed silica 7 wt %, dicyclopentadiene filled microspheres 14 wt % and Grubb's Catalyst 2 wt %.

Example 9

A composition for a glass ionomer cement with self-healing capabilities is described as follows. An aqueous solution that is 47.5% 2:1 polyacrylic acid/itaconic acid copolymer ($M_w$=10,000) and 5% D(+)-tartaric acid is prepared. The powder phase of a typical cement has self-healing fillers added to it. The powder phase consists of 97% calcium fluorosilicate glass ($SiO_2$-29%, $Al_2O_3$-16.6%, $CaF_2$-34.3%, $Na_3AlF_6$-5%, $AlF_3$-5.3%, $AlPO_4$-9.8%), 2.5% dicyclopentadiene filled microspheres and 0.5% Grubb's Catalyst.

Example 10

A composition for a glass ionomer cement with self-healing capabilities is described as follows. An aqueous solution that is 47.5% 2:1 polyacrylic acid/itaconic acid copolymer ($M_w$=10,000) and 5% D(+)-tartaric acid is prepared. The powder phase of a typical cement has self-healing fillers added to it. The powder phase consists of 85% calcium fluorosilicate glass ($SiO_2$-29%, $Al_2O_3$-16.6%, $CaF_2$-34.3%, $Na_3AlF_6$-5%, $AlF_3$-5.3%, $AlPO_4$-9.8%), 14% dicyclopentadiene filled microspheres and 1% Grubb's Catalyst.

Example 11

A composition for a denture base material with self-healing capabilities is described as follows. A liquid component was prepared consisting of 92.5 wt % methyl methacrylate, 2 wt % dibutyl phthalate, 3 wt % ethyl-4-dimethylaminobenzoate, 0.05 wt % hydroquinone, 2 wt % ethylene glycol dimethacrylate. The typical powder phase of a denture base material was modified with fillers capable of self-healing. The powder phase consists of 96 wt % poly(methylmethacrylate), 1.5 wt % benzoyl peroxide, 2 wt % dicyclopentadiene filled microspheres and 0.5 wt % Grubb's catalyst.

Example 12

A composition for a denture base material with self-healing capabilities is described as follows. A liquid component was prepared consisting of 92.5 wt % methyl methacrylate, 2 wt % dibutyl phthalate, 3 wt % ethyl-4-dimethylaminobenzoate, 0.05 wt % hydroquinone, 2 wt % ethylene glycol dimethacrylate. The typical powder phase of a denture base material was modified with fillers capable of self-healing. The powder phase consists of 82 wt % poly(methylmethacrylate), 1.5 wt % benzoyl peroxide, 15 wt % dicyclopentadiene filled microspheres and 1.5 wt % Grubb's catalyst.

Example 13

A composition for a denture reline with self-healing capabilities is described as follows. A liquid-powder type reline formulation includes a powder component of polyethylmethacrylate and a liquid component of Di-n-butyl phthalate, ethyl acetate and ethyl alcohol. The two components are mixed together until all of the powder particles are totally moistened. 2 wt % dicyclopentadiene filled microspheres and 0.5 wt % Grubb's catalyst are added to the mixture and blended in.

Example 14

A composition for a denture reline with self-healing capabilities is described as follows. A liquid-powder type reline formulation includes a powder component of polyethylmethacrylate and a liquid component of Di-n-butyl phthalate, ethyl acetate and ethyl alcohol. The two components are mixed together until all of the powder particles are totally moistened. 15 wt % dicyclopentadiene filled microspheres and 1.5 wt % Grubb's catalyst are added to the mixture and blended in.

Example 15

A composition for a dental appliance (retainer) with self-healing capabilities is described as follows. A thermoplastic fiber-reinforced composite material was prepared using polyethylene terephthalate glycol as the matrix material and glass filaments as the fiber component. 2 wt % dicyclopentadiene filled microspheres and 0.5 wt % Grubb's catalyst are added to the mixture and blended in. Using the resultant composite mixture, retainers were formed on a plaster cast of a dental arch.

Example 16

A composition for a dental appliance (retainer) with self-healing capabilities is described as follows. A thermoplastic fiber-reinforced composite material was prepared using polyethylene terephthalate glycol as the matrix material and glass filaments as the fiber component. 15 wt % dicyclopentadiene filled microspheres and 1.5 wt % Grubb's catalyst are added to the mixture and blended in. Using the resultant composite mixture, retainers were formed on a plaster cast of a dental arch.

Example 17

A composition for a dental bridge with self-healing capabilities is described as follows. The fiber reinforced composite structural component of the dental bridge is comprised of 66 wt % ethoxylated bisphenol A dimethacrylate, 28.7 wt % the polycarbonate dimethacrylate condensation product of triethylene glycol bischloroformate and 2-hydroxyethylmethacrylate, 0.75 wt % camphoroquinone, 1.5 wt % 4-octyloxy-phenyl-phenyl iodonium hexafluoroantimonate, 0.05 wt % 4-methoxyphenol, 2.5 wt % dicyclopentadiene filled microspheres and Grubb's Catalyst 0.5 wt %.

Example 18

A composition for a dental bridge with self-healing capabilities is described as follows. The fiber reinforced composite structural component of the dental bridge is comprised of 56 wt % ethoxylated bisphenol A dimethacrylate, 25.2 wt % the polycarbonate dimethacrylate condensation product of triethylene glycol bischloroformate and 2-hydroxyethylmethacrylate, 0.75 wt % camphoroquinone, 1.5 wt % 4-octyloxy-phenyl-phenyl iodonium hexafluoroantimonate, 0.05 wt % 4-methoxyphenol, 15 wt % dicyclopentadiene filled microspheres and Grubb's Catalyst 1.5 wt %.

Example 19

A composition for a dental inlay with self-healing capabilities is described as follows. Dental inlays are molded from the resultant precursor blend mixture of 37 wt % methyl methacrylate, 0.25 wt % benzoyl peroxide, 8 wt % 2,2-bis(4-methacryloxyphenyl)propane, 34.25 wt % poly(methyl methacrylate-co-ethylene dimethacrylate), 17 wt % poly(m- ethyl methacrylate), 0.5 wt % pigment, 2.5 wt % dicyclopentadiene filled microspheres and Grubb's Catalyst 0.5 wt %.

Example 20

A composition for a dental inlay with self-healing capabilities is described as follows. Dental inlays are molded from the resultant precursor blend mixture of 35 wt % methyl methacrylate, 0.25 wt % benzoyl peroxide, 7.5 wt % 2,2-bis (4-methacryloxyphenyl)propane, 30.25 wt % poly(methyl methacrylate-co-ethylene dimethacrylate), 10 wt % poly(methyl methacrylate), 0.5 wt % pigment, 15 wt % dicyclopentadiene filled microspheres and Grubb's Catalyst 1.5 wt %.

Example 21

A composition for a dental veneer with self-healing capabilities is described as follows. A blend used to prepare dental veneers comprises 3 wt % methyl methacrylate, 0.5 wt % benzoyl peroxide, 47 wt % UDMA, 49.5 wt % poly(methyl methacrylate-co-ethylene dimethacrylate). To this blend solid fillers containing 96 wt % silane treated silica, 1 wt % acrylic acid, 2.5 wt % dicyclopentadiene filled microspheres and Grubb's Catalyst 0.5 wt %. The mixture is then stored and mixed with pigment to make a uniform paste.

Example 22

A composition for a dental veneer with self-healing capabilities is described as follows. A blend used to prepare dental veneers comprises 3 wt % methyl methacrylate, 0.5 wt % benzoyl peroxide, 47 wt % UDMA, 49.5 wt % poly(methyl methacrylate-co-ethylene dimethacrylate). To this blend solid fillers containing 82.5 wt % silane treated silica, 1 wt % acrylic acid, 15 wt % dicyclopentadiene filled microspheres and Grubb's Catalyst 1.5 wt %. The mixture is then stored and mixed with pigment to make a uniform paste.

Example 23

A composition for a dental resin composite with self-healing capabilities is described as follows. A resin mixture (16 wt % total) was first made by combining bisphenol-A-glycidyldimethacrylate (Bis-GMA) resin with triethylene glycol dimethacrylate (TEGDMA) resin in a 7/3 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, Bis-GMA filled microspheres 3.0 wt %.

Example 24

A composition for a dental resin composite with self-healing capabilities is described as follows. A resin mixture (40 wt % total) was first made by combining bisphenol-A-glycidyldimethacrylate (Bis-GMA) resin with triethylene glycol dimethacrylate (TEGDMA) resin in a 7/3 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (60 wt % total): silanated strontium glass 45 wt %, fumed silica 5 wt %, 5 wt % hydroxyfunctional polydimethylsiloxane and vinyltrimethoxyethoxysilane (95:5 ratio) filled microspheres and 5 wt % stannous octooate filled microspheres.

The invention has been described with reference to certain described embodiments. Examples of certain embodiments are listed below. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:
1. A dental composition, comprising:
a first monomer, wherein said first monomer includes one or more monomers selected from the group consisting of: 2,2-bis[4-(2-hydroxy-3-methacryloyloxypropoxy) phenyl]propane (Bis-GMA), dimethacryloxyethyl 2,2,4-trimethylhexamethylene diurethane (UDMA), 1,6-bis-[2-methacryloxy-ethoxycarbonylamino]-2,2,4-trimethylhexane (UEDMA), triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DEGDMA), hexanediol dimethacrylate (HDMA), hexanediol diacrylate (HDDA), trimethylolpropanetriacrylate (TMPTA), trimethylolpropanetrimethacrylate (TMPTMA), ethoxylated trimethylolpropanetriacrylate (EOTMPTA), ethoxylated bisphenol A dimethacrylate (EBPADMA), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth) acrylate; decanediol dimethacrylate; 1,12-dodecanediol di(meth)acrylate; trimethylolpropane mono-(meth) acrylate; trimetfhylolpropane di-(meth)acrylate, trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-(meth)acrylate; sorbitol tri-(meth)acrylate; sorbitol tetra-(meth)acrylate; sorbitol penta-(meth)acrylate; sorbitol hexa-(meth)acrylate; tetrahydrofurfuryl (meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethylisocyanurate trimethacrylate, glycerol phosphate monomethacrylates; glycerol phosphate dimethacrylates; hydroxyethyl methacrylate phosphates; 2-hydroxypropyl(meth)acrylate; citric acid dimethacrylates; citric acid tri-methacrylates; fluoropolymer-functional (meth)acrylates; poly(meth)acrylated polymaleic acid; poly(meth)acrylated polycarboxylpolyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth)acrylate polysiloxanes,
where the siloxane-functional (meth)acrylate polysiloxanes are defined as products resulting from hydrolytic polycondensation of one or more of the following silanes: bis[2-(2-(methacryloyl oxyethoxycarbonyp- ethyl)]-3-triethoxysily-lpropyl amine, bis[2-(2(1)-(methacryloyloxypropoxycarbonyl(ethyl)]-3-triet-hoxysilylpropyl amine, 1,3(2)-dimethacryloyloxypropyl-[3-(3-triethoxysilyl-propyl)aminocarbonyl]propionate, 1,3(2)dimethacryloyloxypropyl-[4-(3-trie-thoxysilyl propyl)aminocarbonyl]butyrate, 1,3(2)dimethacryloyloxypropyl-[-4-(3-triethoxysilylpropyl)-N-iethylaminocarbonyl]butyrate, 3-[1,3(2)dimethacryloyloxypropyl)-2(3)-oxycarbonylamido]-propyltriethoxysilane, glycerol phosphate monomethacrylates, glycerol phosphate dimethacrylates, hydroxyethyl methacrylate phosphates, citric acid di-methacrylates, citric acid tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids;

a polymerization initiator; and a microsphere encapsulating a second monomer, wherein said second monomer is released from said microsphere and polymerized by said polymerization initiator; wherein said first monomer is present outside said microsphere and, optionally, inside said microsphere.

2. The dental composition of claim 1, wherein said second monomer includes one or more monomers selected from the group consisting of:

bis-3,4-epoxycyclohexylethylphenylmethylsilane, 3,4-epoxycyclohexylethylcyclopolymethylsiloxane, 2,2-bis[4-(2-hydroxy-3-methacryloyloxypropoxy)phenyl]propane (Bis-GMA), dimethacryloxyethyl 2,2,4-trimethylhexamethylene diurethane (UDMA), 1,6-bis-[2-methacryloxy-ethoxycarbonylamino]-2,2,4-trimethylhexane (UEDMA), triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DEGDMA), hexanediol dimethacrylate (HDMA), hexanediol diacrylate (HDDA), trimethyloipropanetriacrylate (TM PTA), trimethylolpropanetrimethacrylate (TMPTMA), ethoxylated trimethylolpropanetriacrylate (EOTMPTA) and ethoxylated bisphenol A dimethacrylate (EBPADMA).

3. The dental composition of claim 1, wherein said microsphere accounts for about 2.5-14 wt % of a dental restorative composite.

4. A dental composition, comprising:

a first monomer, wherein said first monomer includes one or more monomers selected from the group consisting of: 2,2-bis[4-(2-hydroxy-3-methacryloyloxypropoxy)phenyl]propane (Bis-GMA), dimethacryloxyethyl 2,2,4-trimethylhexamethylene diurethane (UDMA), 1,6-bis-[2-methacryloxy-ethoxycarbonylamino]-2,2,4-trimethylhexane (UEDMA), triethyleneglycol dimethacrylate (TEGDMA), polyethylene glycol dimethacrylate (PEGDMA), glyceroldimethacrylate (GDM), methacryloyloxyethyl maleate (MEMA), diethyleneglycol dimethacrylate (DEGDMA), hexanediol dimethacrylate (HDMA), hexanediol diacrylate (HDDA), trimethyloipropanetriacrylate (TMPTA), trimethylolpropanetrimethacrylate (TMPTMA), ethoxylated trimethylolpropanetriacrylate (EOTMPTA), ethoxylated bisphenol A dimethacrylate (EBPADMA), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono-(meth)acrylate; di-(meth)acrylate, trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-penta-(meth)acrylate, di-penta-(meth)acrylate, tri-penta-(meth)acrylate, tetra-penta-(meth)acrylate, penta-(meth)acrylate; sorbitol hexa-(meth)acrylate; tetrahydrofurfuryl (meth)acrylate; bis[1-(2-acryloxy)]-p-ethoxyphenyldimethylmethane; bis[1-(3-acryloxy-2-hydroxy)]-ppropoxyphenyldimethylmethane; 2,2,4-trimethylhexamethylene diisocyanate; tris-hydroxyethylisocyanurate trimethacrylate, glycerol phosphate monomethacrylates; glycerol phosphate dimethacrylates; hydroxyethyl methacrylate phosphates; 2-hydroxypropyl(meth)acrylate; citric acid di-methacrylates; citric acid tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly(meth)acrylated polyboric acid; polymerizable bisphosphonic acids, and siloxane-functional (meth)acrylate polysiloxanes, where the siloxane-functional (meth)acrylate polysiloxanes are defined as products resulting from hydrolytic polycondensation of one or more of the following silanes: bis[2-(2-(methacryloyl oxyethoxycarbonyl (ethyl)]-3-'itriethoxysily-lpropyl amine, bis[2-(2(1)-(methacryloyloxypropoxycarbonyl)ethyl)]-3-triet-hoxysilylpropyl amine, 1,3(2)dimethacryloyloxypropyl-[3-(3-triethoxysilyl-propyl)aminocarbonyl]propionate, 1,3(2)dimethacryloyloxypropyl-[4-(3-trie-thoxysilyl propyl)aminocarbonyl]butyrate, 1,3(2)-dimethacryloyloxypropyl-[-4-(3-triethoxysilylpropyl)-N-'iethylaminocarbonyl]butyrate, 3-[1,3(2)dimethacryloyloxypropyl)-2(3)-oxycarbonylamidol]'propyltriethoxysilane, glycerol phosphate monomethacrylates, glycerol phosphate dimethacrylates, hydroxyethyl methacrylate phosphates, citric acid di-methacrylates, tri-methacrylates, poly(meth)acrylated oligomaleic acid, poly(meth)acrylated polymaleic acid, poly(meth)acrylated poly (meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids;

a polymerization initiator;

a catalyst; and a first microsphere encapsulating a second monomer, wherein said second monomer is released from said first microsphere and polymerized by said catalyst wherein said first monomer is present outside said microsphere and, optionally, inside said microsphere.

5. The dental composition of claim 4, wherein said second monomer includes one or more monomers selected from the group consisting of:

cyclopentadienes; norbornenes; norbornadienes; 7-oxonorbornenes; azanorbornenes; cyclobutenes; cyclooctenes; cyclooctodienes; cyclooctatetraenes; acyclic dienes; and acetylenes.

6. The dental composition of claim 4, wherein said catalyst is encapsulated in a second microsphere.

7. The dental composition of claim 4, wherein said catalyst is a olefin metathesis catalyst.

8. The dental composition of claim 7, wherein said olefin metathesis catalyst is a Grubb's catalyst.

9. The dental composition of claim 4, wherein said first microsphere accounts for about 2.5-14 wt % of the dental composition.

10. The dental composition of claim 4, wherein said catalyst accounts for about 0.5-2 wt % of the dental composition.

* * * * *